United States Patent
Binia et al.

(10) Patent No.: US 11,083,742 B2
(45) Date of Patent: *Aug. 10, 2021

(54) HUMAN MILK OLIGOSACCHARIDES FOR HEALTH BENEFITS BY PREVENTION OF PREMATURE ADIPOSITY REBOUND

(71) Applicant: NESTEC S.A., Vevey (CH)

(72) Inventors: Aristea Binia, Fribourg (CH); Norbert Sprenger, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/071,731

(22) PCT Filed: Jan. 26, 2017

(86) PCT No.: PCT/EP2017/051589
§ 371 (c)(1),
(2) Date: Jul. 20, 2018

(87) PCT Pub. No.: WO2017/129648
PCT Pub. Date: Aug. 3, 2017

(65) Prior Publication Data
US 2019/0015436 A1  Jan. 17, 2019

(30) Foreign Application Priority Data
Jan. 26, 2016  (EP) .................... 16152738

(51) Int. Cl.
*A61K 31/702* (2006.01)
*A23L 33/00* (2016.01)
*A23L 33/21* (2016.01)
*A61P 3/04* (2006.01)

(52) U.S. Cl.
CPC ............ *A61K 31/702* (2013.01); *A23L 33/21* (2016.08); *A23L 33/40* (2016.08); *A61P 3/04* (2018.01); *A23V 2002/00* (2013.01)

(58) Field of Classification Search
CPC ........ A61K 31/702; A23L 33/21; A23L 33/40
See application file for complete search history.

(56) References Cited

U.S. PATENT DOCUMENTS

| | | | |
|---|---|---|---|
| 6,146,670 A * | 11/2000 | Prieto ...................... | A23L 33/40 426/72 |
| 2011/0110904 A1 | 5/2011 | Fichot et al. | |
| 2012/0171166 A1* | 7/2012 | Chow .................... | A23L 33/135 424/93.4 |
| 2019/0029302 A1* | 1/2019 | Binia ...................... | A23L 33/125 |
| 2019/0029303 A1* | 1/2019 | Binia ...................... | A61K 45/06 |
| 2019/0029308 A1* | 1/2019 | Binia ...................... | A23L 33/21 |
| 2019/0046545 A1* | 2/2019 | Binia ........................ | A61P 3/04 |

FOREIGN PATENT DOCUMENTS

| CN | 103391783 A | 11/2013 |
|---|---|---|
| EP | 2497478 A2 | 9/2012 |

OTHER PUBLICATIONS

Asakuma (European Journal of Clinical Nutrition; 2008, 62, 488-494).*
Grummer-Strawn et al. "Does Breastfeeding Protect Against Pediatric Overweight? Analysis of Longitudinal Data From the Centers for Disease Control and Prevention Pediatric Nutrition Surveillance System" Pediatrics, Feb. 2004, vol. 113, No. 2, pp. e81-e86.
Alderete et al. "Associations between human milk oligosaccharides and infant body composition in the first 6 mo of life" Am J Clin Nutr, 2015, vol. 102, pp. 1361-1368.
Pedersen et al, "Polyunsaturated fatty acid content of mother's milk is associated with childhood body composition" Pediatric Research, Dec. 2012, vol. 72, No. 6, pp. 631-636.
Mills et al. "Milk intelligence: Mining milk for bioactive substances associated with human health" International Dairy Journal, 2011, vol. 21, pp. 377-401.
Madsen et al. "IGF-1 and IGFBP-3 in healthy 9 month old infants from the SKOT cohort: Breastfeeding, diet, and later obesity" Growth Hormone & IGF Research, 2011, vol. 21, pp. 199-204
Yu et al. "The principal fucosylated oligosaccharides of human milk exhibit prebiotic properties on cultured infant microbiota" Glycobiology, 2013, vol. 23, No. 2; pp. 169-177.
Von Kries et al. "Breast feeding and obesity: cross sectional study" BMJ, 1999, vol. 319, pp. 147-150.
Gillman "Breast-feeding and obesity" The Journal of Pediatrics, Dec. 2002, vol. 141, No. 6, pp. 749-750.
Wall "Outcomes of Breastfeeding Versus Formula Feeding" Evergreen Perinatal Education, Oct. 2013, 66 pages.
EFSA Panel on Dietetic Products, Nutrition and Allergies (NDA) Scientific Opinion Entitled "Statement on the safety of lacto-N-neotetraose and 2'-O-fucosyllactose as novel food ingredients in food supplements for children" EFSA Journal, 2015, vol. 13, No. 11, 11 pages.
Campbell et al. "The predictors of early adiposity rebound" Early Human Development, 2007, vol. 83, p. S159.
Hongxin et al., "Recent Progress in Research on Composition and Functions of Human Milk Oligosaccharides", Journal of Dairy Science and Technology, vol. 38, Issue No. 3, Dec. 31, 2015, pp. 30-33.
Office Action Received for Application No. CN201780007746.7, dated Aug. 3, 2020, 11 pages(3 Pages of English Translation and 8 Pages of Official Copy).
Castanys-Munoz et al., "2'-fucosyllactose: An Abundant, Genetically Determined Soluble Glycan Present in Human Milk", Nutrition Reviews, 2013, vol. 71, Issue No. 12, pp. 773-789, XP055271416.
Russia Patent Office Action for Application No. 2018130472, dated Feb. 16, 2021, 17 Pages.

* cited by examiner

*Primary Examiner* — Pancham Bakshi
(74) *Attorney, Agent, or Firm* — K&L Gates LLP

(57) ABSTRACT

The present invention relates to a nutritional composition comprising at least one fucosylated oligosaccharide for use in an infant or young child for preventing a later in life health disorder by preventing premature adiposity rebound. The invention also relates to nutritional composition for use to promote healthy growth.

13 Claims, 2 Drawing Sheets

HUMAN MILK OLIGOSACCHARIDES FOR HEALTH BENEFITS BY PREVENTION OF PREMATURE ADIPOSITY REBOUND

CROSS REFERENCE TO RELATED APPLICATIONS

The present application is a National Stage of International Application No. PCT/EP2017/051589, filed on Jan. 26, 2017, which claims priority to European Patent Application No. 16152738.7, filed on Jan. 26, 2016, the entire contents of which are being incorporated herein by reference.

TECHNICAL FIELD OF THE INVENTION

The present invention relates to nutritional compositions for use in an infant or young child for preventing a later in life health disorder by preventing premature adiposity rebound.

BACKGROUND OF THE INVENTION

The prevalence of obesity and overweight in adults, children and adolescents has increased rapidly over the past 30 years globally and continues to rise. Worldwide obesity has more than doubled since 1980, as reported by the WHO. It has become a global health concern since it is associated with a reduced life time, an altered life quality and it is responsible for further health conditions. Overweight and obesity are linked to more deaths worldwide than underweight. Childhood obesity is indeed associated with a higher chance of obesity, premature death and disability in adulthood. But, in addition to increased future risks, obese children experience breathing difficulties, increased risk of fractures, hypertension, early markers of cardiovascular disease, insulin resistance and psychological effects. Raised BMI is a major risk factor for non-communicable diseases such as cardiovascular diseases (mainly heart disease and stroke), which were the leading cause of death in 2012; diabetes; musculoskeletal disorders (especially osteoarthritis—a highly disabling degenerative disease of the joints); and even some cancers (endometrial, breast, and colon).

Mother's milk is recommended for all infants for various reasons. Breastfeeding has especially been reported to be beneficial for prevention against obesity in comparison to formula feeding (Owen et al, Effect of Infant Feeding on the Risk of Obesity Across the Life Course: A Quantitative Review of Published Evidence, 2005). Evidence suggests that infancy may be a critical period in the development and programming of obesity or future metabolic diseases. It has been widely reported that breast-fed infants do have a different growth pattern than infants fed with infant formula. Indeed, breast-fed infants have a lower weight gain and a lower body fat mass within the first year of life as compared to formula fed infants. Additionally, breast-fed infants have a different gut microbiota profile as compared to infant fed with infant formula. Altogether, these factors affect the development of the infant physiology, including metabolism, immunity and overall growth.

However, in some cases breastfeeding is inadequate or unsuccessful for medical reasons or the mother chooses not to breast feed. Infant formula have been developed for these situations. Fortifiers have also been developed to enrich mother's milk or infant formula with specific ingredients. It is known that the growth rate in infants influence later risk of excessive fat mass accumulation and related metabolic and cardiovascular diseases. In particular, a faster growth rate in infancy may predispose that infant to obesity later in life.

Hence, nutritional compositions which contribute to healthy growth in infant and young children, and which can contribute to preventing excessive fat mass accumulation, would be advantageous.

There is clearly a need to deliver such health benefits in a manner that is particularly suitable for young subjects (infants and young children) and in a manner that does not involve a classical pharmaceutical intervention as these subjects are particularly fragile.

There is a need to deliver such health benefits in the infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

SUMMARY OF THE INVENTION

Thus, one aspect of the invention relates to a nutritional composition comprising at least one fucosylated oligosaccharide, for use in an infant or young child in preventing a later in life health disorder, such as later in life excessive fat mass accumulation; and/or a health disorder related to excessive fat mass accumulation, such as later in life overweight, obesity and/or obesity-related comorbidities, by preventing premature adiposity rebound.

Another aspect of the present invention relates to the use of a nutritional composition according to the invention for reducing the risk of development of overweight later in life in an infant or a young child by preventing premature adiposity rebound.

DESCRIPTION OF THE INVENTION

Definitions

Figure 1:
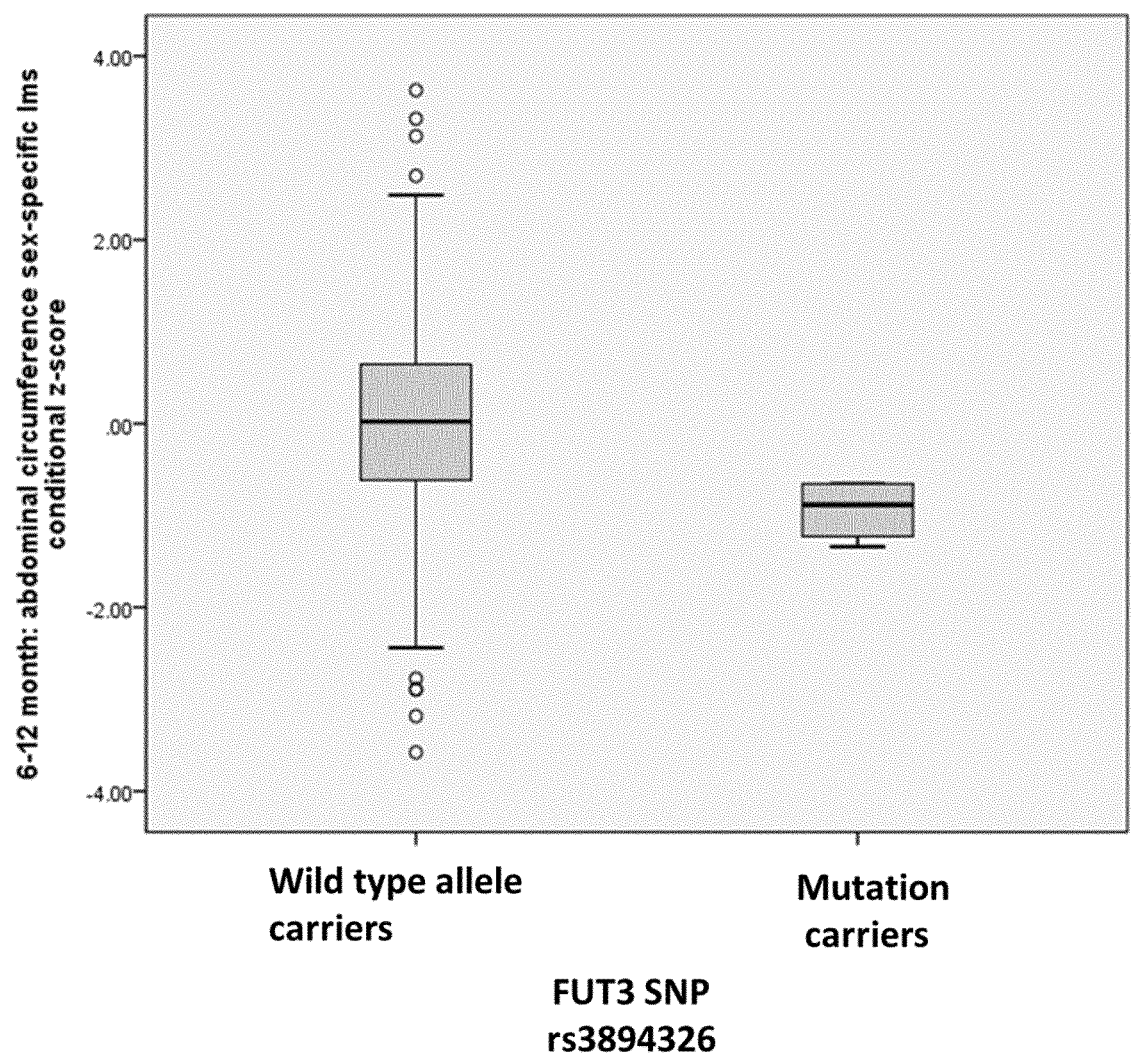
FIG. 1 shows the abdominal circumference sex-specific LMS conditional z-score for 6-12 months for the polymorphism FUT3 rs3894326.

Prior to discussing the present invention in further details, the following terms, expressions and conventions will first be defined:

Fucose is a hexose deoxy sugar with the chemical formula $C_6H_{12}O_5$. It corresponds to 6-deoxy-L-galactose.

Fucosyltransferases (also known as glycosyltransferase family 10) are enzymes which transfer an L-fucose sugar from a GDP-fucose (guanosine diphosphate-fucose) donor substrate to an acceptor substrate.

Fucosyltransferase 3 (abbreviated herein as FUT3), is also known as Galactoside 3(4)-L-fucosyltransferase. Further synonyms include CD174; FT3B; FucT-III, LE; and Les. EC number is 2.4.1.65 and OMIM number: 111100. HomoloGene: 55438 ChEMBL: 3269 GeneCards: FUT3 Gene.

The FUT3 gene encodes an enzyme with alpha (1,3)-fucosyltransferase and alpha(1,4)-fucosyltransferase activities.

Fucosyltransferase 2 (abbreviated herein as FUT2), is also known as Galactoside 2-alpha-L-fucosyltransferase 2, EC 2.4.1.69, SE 2, SEC2, Fucosyltransferase-2 (secretor), GDP-L-fucose:beta-D-galactoside 2-alpha-L-fucosyltransferase 2, Galactoside 2-alpha-L-fucosyltransferase 2, Secretor blood group alpha-2-fucosyltransferase, Secretor factor, and transmembrane protein 2. The FUT2 gene is also referred to in the art as the secretor gene (Se).

A SNP (single nucleotide polymorphism) is a variation in a single nucleotide which may occur at some specific position in the genome, where each variation is present to some appreciable degree within a population. Functional SNPs, such as the ones described in the present invention, affect protein expression.

The term "infant" means a person under the age of 12 months.

The expression "young child" means a person aged from one to three years, also called toddler.

The term "child" means a person aged over three years to 12 years of age.

A person over 12 years of age to 18 years of age is referred to as an adolescent, and a person aged over 18 years is referred to as an adult.

The expression "nutritional composition" means a composition which nourishes a subject. This nutritional composition is usually to be taken orally or intravenously. It may include a lipid or fat source, a carbohydrate source and/or a protein source.

In a particular embodiment the composition of the present invention is a hypoallergenic nutritional composition. The expression "hypoallergenic nutritional composition" means a nutritional composition which is unlikely to cause allergic reactions.

In a particular embodiment the nutritional composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic nutritional composition is not breast milk).

The expression "infant formula" as used herein refers to a foodstuff intended for particular nutritional use by infants during the first months of life (such as from 0 to 12 months, 0 to months, 0 to 8 months, 0 to 6 months or 0 to 4 months) and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

A "growing-up milk" (or GUM) is generally a milk-based adapted for the specific nutritional needs of a toddler or young child.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The term "supplement" refers to a nutritional composition intended to provide nutrients that may otherwise not be consumed in sufficient quantities. It is taken in addition to other nutrition/food. It may be in the form of tablets, capsules, pastilles or a liquid for example. The supplement may further contain protective hydrocolloids (such as gums, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. The term "complement" means the same as supplement, and the terms can be used interchangeably herein.

The expressions "fat mass accumulation" and "fat accumulation" can be used interchangeably.

The expression "excessive fat mass accumulation" refers to abnormal fat mass body amount, e.g. in an amount that may impair health and can lead to health disorders. Being overweight or obese are examples of having excessive fat accumulation.

Body mass index (BMI) is a simple index of weight-for-height that is commonly used to classify overweight and obesity. BMI is defined as a person's weight in kilograms divided by the square of his height in meters (kg/m2). According to the WHO, a BMI greater than or equal to 25 is overweight; a BMI greater than or equal to 30 is obesity.

The expressions "reducing (excessive) fat mass accumulation" and "avoiding (excessive) fat mass accumulation" refer to a decrease or a limitation of the body fat amount of an individual.

The expression "health disorder(s)" encompass any health conditions and/or diseases and/or dysfunctions that affect the organism of an individual, including the metabolic ones.

The expressions "preventing a health disorder later in life" or "preventing a later in life health disorder" can be used interchangeably. They mean avoiding that a health disorder (e.g. obesity) occur later in life and/or decreasing the incidence and/or the severity of a health disorder later in life. The prevention occurs "later in life", so preferably after the termination of the intervention or treatment (i.e. after administration of the nutritional composition according to the invention).

The expression "later in life health disorder related to excessive fat mass accumulation" refers to later in life health disorder due to (i.e., direct link) or associated with (i.e., indirect link) fat excess. It encompasses overweight, obesity and obesity related comorbidities.

The expression "obesity related comorbidities" include hypertension, dyslipidemia, insulin resistance, type 2 diabetes, sleep apnea, arthritis, hyperuricemia, gall bladder disease, cardiovascular disease, metabolic syndrome and certain types of cancer.

The prevention occurs "later in life", for example after administration of the nutritional composition according to the invention, or for example after the termination of the intervention or treatment.

The expression "later in life" and "in later life" can be used interchangeably. Effects which occur "later in life"/"in later life" refers to effects measured in the individual (infant or young child) after the administration of the nutritional composition according to the invention, and after at least 8 months or after some years after birth, such as after the age of 8 months after birth, such as after the age of 10 months after birth, such as after the age of 1 year after birth, such as after the age of 2 years, preferably after the age of 4 years, more preferably after the age of 5 years, even more preferably after the age of 7 years after birth, or even more, and as a comparison to average observations for subjects of the same age. Preferably it refers to an effect observed after at least 1 year of life, or after at least 2, 5, 7, or 15 years of life. So the expression "later in life" might refer to an observation during infancy, during early childhood, during childhood, during the adolescent period, or during adulthood. Preferably, it refers to an observation during childhood, during the adolescent period, or during adulthood.

The expression "mother's milk" should be understood as the breast milk or the colostrum of the mother.

The expression "HMO" or "HMOs" refers to human milk oligosaccharide(s). These carbohydrates are resistant to enzymatic hydrolysis by digestive enzymes (e.g pancreatic and/or brush border), indicating that they may display functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2'-fucosyllactose), 3-FL (3'-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

An "alpha 1,3 fucosylated oligosaccharide" is an oligosaccharide having a fucose linked via the C1 of fucose in alpha conformation to a C3 of a monosaccharide unit of a mono-, or oligosaccharide (2 or more monosaccharides).

An "alpha 1,4 fucosylated oligosaccharide" is an oligosaccharide having a fucose linked via the C1 of fucose in alpha conformation to a C4 of a monosaccharide unit of a mono-, or oligosaccharide (2 or more monosaccharides).

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) or any combination thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or follow-on/follow-up formula or infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. Dietary modulation of the human colonic microbiota: introducing the concept of prebiotics. J Nutr. 1995; 125:1401-12).

The term "probiotic" means microbial cell preparations or components of microbial cells with a beneficial effect on the health or well-being of the host. (Salminen S, Ouwehand A. Benno Y. et al. "Probiotics: how should they be defined" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

DESCRIPTION OF INVENTION

Basis of the Invention

The present invention is based on the recognition of the importance of fucosylated oligosaccharides in the diet of an infant for the timing of adiposity rebound (defined below). Mothers who display single nucleotide polymorphisms (SNPs) disrupting the expression of FUT3 (the gene encoding fucosyltransferase 3), also display reduced amounts of alpha 1,3 and alpha 1,4 fucosylated oligosaccharides in breast milk. The inventors have shown that, surprisingly, the presence of this particular SNP is significantly linked with abdominal circumference measurements of infants and young children (see Example and Table 3).

The implication is that fucosylated human milk oligosaccharides, such as alpha 1,3 fucosylated oligosaccharides and alpha 1,4 fucosylated oligosaccharides (such as fucosylated oligosaccharide fucosylated by FUT3), influence infant growth by influencing the timing of adiposity rebound.

Adiposity rebound is defined in the context of the present invention as the point in the development of an individual, where BMI begins to rise after infancy. Normally an infant will gain weight during the earliest period of life). This is followed by a period in development of the infant/young child where BMI decreases. The decrease in BMI is typically due to the increased growth in length, and possibly also to decreased fat accumulation. At a certain time point in development, the BMI will stop decreasing, and again begin to rise. This point in time when BMI starts to rise after infancy is known as adiposity rebound (AR). The term adiposity rebound is an accepted term in the field, and has been described for example in Rolland-Cahera et al, Am J Clin Nutr. 1984 January; 39(1):129-35.

Premature adiposity rebound is linked to excessive accumulation of fat later in life, for example in adolescence and/or adulthood. Young children who display a premature adiposity rebound (i.e., adiposity rebound which occurs earlier than expected), have an increased risk of overweight, obesity, and obesity related comorbidities later in life.

There have been previous investigations regarding fucosylated human milk oligosaccharides and growth. For example, Alderete et al have studied human milk oligosaccharides early in development (Alderete et al, Am J Clin Nutr. 2015 December; 102(6):1381-8). However, the conclusions that can be drawn from this study are limited to the period 0 to 6 months which were studied, and no inferences can be made as to the influence of human milk oligosaccharides on the risks for occurrence of excessive fat mass accumulation later in life, nor to the timing of adiposity rebound. Indeed, the authors themselves conclude as much.

Furthermore, the effect of fucosylated oligosaccharides documented in Alderete et al is varied depending on the type of fucosylated oligosaccharides. For example, alpha 1,3 fucosylated oligosaccharides and alpha 1,4 fucosylated oligosaccharides such as LNFPII have been associated with fat increase at 6 months. The opposite was obtained for fucosylated oligosaccharides not having this type of linkage (e.g. LNFPI, LNnT). One skilled in the art would therefore not have been incited to select alpha 1,3 fucosylated oligosaccharides and alpha 1,4 fucosylated oligosaccharides (such as fucosylated oligosaccharide fucosylated by FUT3) to avoid later in life health disorders, by preventing premature adiposity rebound. However the inventors of the present invention shown that these particular oligosaccharides were in fact able to avoid premature adiposity rebound and therefore prevent later in life excessive accumulation of fat or disorders associated thereof.

Acting on premature adiposity rebound represent new clinical situations where prevention of later in life health disorder can be targeted in a new way.

Nutritional Composition for Use

Thus the invention in a first aspect relates to a nutritional composition comprising at least one fucosylated oligosaccharide for use in an infant or young child in preventing a later in life health disorder, such as a later in life excessive fat mass accumulation; and/or a health disorder related to excessive fat mass accumulation, such as later in life obesity and/or obesity-related comorbidities, by preventing premature adiposity rebound.

The nutritional compositions according to the invention prevent premature adiposity rebound, and thereby protect the subject from excessive fat mass accumulation, and/or from a later in life health disorder related to excessive fat mass accumulation, such as later in life obesity and related comorbidities.

The nutritional compositions of the invention are typically administered to an infant or a young child; however the effect of preventing later in health disorder may be seen first later in life.

In the context of this application "later in life" means later in the life of the same infant or young child to whom the nutritional composition was administered. Thus, the nutritional composition for use according to the invention may be administered to an infant or young child, and may contribute to preventing health disorders which otherwise might appear later in that infant's or young child's life. Later in life in this context may mean for example, at any point when the infant or young child is no longer a young child, for example the infant or young child may have become a child, adolescent or adult. See also Definitions for further discussion of the expression "later in life".

In one embodiment the nutritional composition according to the invention may be for use in reducing and/or preventing excessive fat mass accumulation in an infant or young child, by preventing premature adiposity rebound. By this is meant that the nutritional composition according to the invention is administered to an infant or young child and prevents excessive fat mass accumulation in said infant or young child by preventing premature adiposity rebound.

In another embodiment, the nutritional composition according to the invention may be for use in an infant or young child for reducing and/or preventing excessive fat mass accumulation later in life, by preventing premature adiposity rebound. By this is meant that the nutritional composition according to the invention is administered to an infant or young child and prevents excessive fat mass accumulation later in life of the said infant or young child, by preventing premature adiposity rebound.

In a further embodiment, the nutritional composition according to the invention may be for use in an infant or young child for use in preventing a later in life health disorder, for example a health disorder related to excessive fat mass accumulation, by preventing premature adiposity rebound. By this is meant that the nutritional composition according to the invention is administered to an infant or young child and prevents a health disorder, e.g. a health disorder related to excessive fat mass accumulation, said health disorder occurring later in life of said infant or young child, by preventing premature adiposity rebound.

Fucosylated Oligosaccharides

As mentioned above, the nutritional composition for use according to the invention comprises at least one fucosylated oligosaccharide.

One particular embodiment relates to wherein said fucosylated oligosaccharide has at least one fucose group attached by an alpha 2 linkage, alpha 1,2 linkage, alpha1,3 linkage, alpha 1,4 linkage, or combinations thereof.

In a particular embodiment, said fucosylated oligosaccharide is fucosylated by FUT3 and/or by FUT2. So in a specific embodiments, the invention relates to a nutritional composition for use according to the invention comprising at least one fucosylated oligosaccharide which is fucosylated by FUT3 for use in an infant or young child for reducing and/or avoiding excessive fat mass accumulation, by preventing premature adiposity rebound; and/or for use in an infant or young child for preventing a later in life health disorder, such as a health disorder related to excessive fat mass accumulation, such as later in life obesity and related comorbidities, by preventing premature adiposity rebound.

In one embodiment of the invention, the at least one fucosylated oligosaccharide in the nutritional composition according to the invention is one or more selected from the group consisting of 3' fucosylated lactose (3FL), DFL, LNFP II, LNFP III, LNFP V, LNDFH I, LNDFH II, F-LNH II, F-para-LNH I, F-para-LNH II, DF-LNH II, DF-LNH I, DF-LNnH, DF-para-LNH, DF-para-LNnH, TF-LNH, TF-para-LNH I, TF-para-LNH II, TF-para-LNnH, F-LNO, F-LNnO, F-iso-LNO, DF-LNO I, BF-LNO II, DF-LNnO I, DF-LNnO II, DF-iso-LNO I, DF-iso-LNO II, TF-LNO, TF-LNnO, TF-iso-LNO I, TF-iso-LNO II, Tetra-F-iso-LNO, Tetra-F-para-LNO, Penta-F-iso-LNO, F-LND, F-SL, F-LSTa, F-LSTb, F-LSTd, FS-LNH I, FS-LNH II, FS-LNH III, FS-LNH IV, FS-LNnH I, FS-LNnH II, DFS-LNH I, DFS-LNH II, DFS-LNnH, FS-LNO, FS-iso-LNO, DFS-iso-LNO I, FS-iso-LNO II, DFS-LNO, TFS-iso-LNO, FDS-LNT I, FDS-LNH II, FDS-LNH III, FDS-LNnH, FS-novo-LNP I, DF-para-LNH sulfate I, DF-para-LNH sulfate II, TF-para-LNH sulfate and combinations thereof (see Table 1 for explanations of abbreviations). Reference is also made to 'Oligosaccharides: Sources, Properties and Applications", Nova Science Publishers, 2011; Editor Nicole S Gordon; Chapter 1 relating to Milk Oligosaccharides, and in particular to Table 4 of that chapter, which details the structures of the mentioned oligosaccharides).

Particular embodiments of the nutritional composition for use according to the invention relate to wherein the at least one fucosylated oligosaccharide is selected from the group consisting of 3' fucosylated lactose (3'FL), DFL, LNFP II, LNFP III, LNFP V.

In further particular embodiments of the invention, the at least one fucosylated oligosaccharide is selected from the group consisting of 3' fucosylated lactose (3'FL) and DFL.

The following fucosylated oligosaccharides will be referred to in the following by their abbreviations.

TABLE 1

Fucosylated oligosaccharides trivial names and abbreviations

| Abbreviation | Full name | Alpha 1,3 Linkage | Alpha 1,4 Linkage |
|---|---|---|---|
| 3FL | 3' fucosylated lactose | yes | |
| DFL | diFucosyllactose = lactodifucotetraose | yes | |
| LNFP II | Lacto-N-fucopentaose II | | yes |
| LNFP III | Lacto-N-fucopentaose III | yes | |
| LNFP V | Lacto-N-fucopentaose V | yes | |
| LNDFH I | Lacto-N-Difucohexaose I | | yes |
| LNDFH II | Lacto-N-Difucohexaose I | yes | yes |
| F-LNH II | F-lacto-N-hexaose II | yes | |
| F-para-LNH I | F-para-lacto-N-hexaose II | yes | |
| F-para-LNH II | F-para-lacto-N-hexaose II | | yes |
| DF-LNH II | Difucosyllacto-N-hexaose II | yes | yes |
| DF-LNH I | Difucosyllacto-N-hexaose I | yes | |
| DF-LNnH | Difucosyllacto-N-neohexaose | yes | |
| DF-para-LNH | Difucosyl-para-lactohexaose | yes | yes |
| DF-para-LNnH | Difucosyl-para-lacto-N-neohexaose | yes | yes |
| TF-LNH | Trifucosyllacto-N-hexaose | yes | yes |
| TF-para-LNH I | Trifucosyl-para-lacto-N-hexaose I | yes | yes |
| TF-para-LNH II | Trifucosyl-para-lacto-N-hexaose II | yes | yes |
| TF-para-LNnH | Trifucosyl-para-lacto-N-neohexaose I | yes | |
| F-LNO | Fucosyl-lacto-N-octaose | yes | |
| F-LNnO | Fucosyl-lacto-N-neooctaose | yes | |

TABLE 1-continued

Fucosylated oligosaccharides trivial names and abbreviations

| Abbreviation | Full name | Alpha 1,3 Linkage | Alpha 1,4 Linkage |
|---|---|---|---|
| DF-LNO I | Difucosyl-lacto-N-octaose I | yes | |
| DF-LNO II | Difucosyl-lacto-N-octaose II | yes | yes |
| DF-LNnO I | Difucosyl-lacto-N-neooctaose I | yes | yes |
| DF-LNnO II | Difucosyl-lacto-N-neooctaose II | yes | |
| DF-iso-LNO I | Difucosyl-iso-lacto-N-octaose I | yes | yes |
| DF-iso-LNO II | Difucosyl-iso-lacto-N-octaose II | yes | |
| TF-LNO | Trifucosyl-lacto-N-octaose | yes | yes |
| TF-LNnO | Trifucosyl-lacto-N-neooctaose | yes | yes |
| TF-iso-LNO I | Trifucosyl-iso-lacto-N-octaose I | yes | |
| TF-iso-LNO II | Trifucosyl-iso-lacto-N-octaose II | yes | yes |
| Tetra-F-iso-LNO | Tetra-Fucosyl-iso-lacto-N-octaose | yes | yes |
| Tetra-F-para-LNO | Tetra-Fucosyl-para-lacto-N-octaose | yes | yes |
| Penta-F-iso-LNO | Penta-Fucosyl-iso-lacto-N-octaose | yes | yes |
| F-LND I | Fucosyl-lacto-N-decasaccharide | yes | |
| F-SL | 3' Sialyl-3fucosyllactose | yes | |
| F-LSTa | Fucosyl-LS-Tetrasaccharide a/Sialyl-lacto-N-tetraose a | | yes |
| F-LSTc | Fucosyl-LS-Tetrasaccharide c/Sialyl-lacto-N-tetraose c | yes | |
| FS-LNH I | fucosyl-sialyl-lacto-N-hexaose I | yes | |
| FS-LNH II | fucosyl-sialyl-lacto-N-hexaose II | yes | |
| FS-LNH III | fucosyl-sialyl-lacto-N-hexaose III | | yes |
| FS-LNH IV | fucosyl-sialyl-lacto-N-hexaose IV | | yes |
| FS-LNnH I | fucosylsialyllacto-N-neohexaose I | yes | |
| DFS-LNH I | difucosyl sialyl-lacto-N-hexaose I | | yes |
| DFS-LNH II | difucosyl sialyl-lacto-N-hexaose II | yes | yes |
| DFS-LNnH | difucosyl sialyl-lacto-N-neohexaose | yes | |
| FS-LNO | fucosyl-sialyl-lacto-N-octaose | | yes |
| FS-iso-LNO | fucosyl-sialyl-iso lacto-N-octaose | | yes |
| DFS-iso-LNO I | difucosyl-sialyl-iso-lacto-N-octaose I | yes | yes |
| FS-iso-LNO II | fucosyl-sialyl-iso-lacto-N-octaose II | | yes |
| DFS-LNO | difucosyl-sialyl-lacto-N-octaose | yes | yes |
| TFS-iso-LNO | tri fucosyl-sialyl-lacto-N-octaose | yes | yes |
| FDS-LNT I | Fuco-disialyllacto-N-tetraose | | yes |
| FDS-LNH II | Fuco-disialyllacto-N-hexaose II | yes | |
| FDS-LNH III | Fuco-disialyllacto-N-hexaose II | | yes |
| FDS-LNnH | Fuco-disialyllacto-N-neohexaose II | yes | |
| FS-novo-LNP I | fucosyl-sialyl-novo-lacto-N-pentaose i | yes | |
| DF-para-LNH sulfate I | Difucosyl-para-lacto-N-hexaose sulfate I | yes | |
| DF-para-LNH sulfate II | Difucosyl-para-lacto-N-hexaose sulfate I | yes | yes |
| TF-para-LNH sulfate | Trifucosyl-para-lacto-N-hexaose sulfate | yes | yes |

Yes indicates is present, empty box indicates not present.

Health Disorders and Adiposity Rebound

Further embodiments relate to nutritional composition for use, according to the present invention wherein the health disorder is a health disorder related to excessive fat mass accumulation. The health disorder related to excessive fat mass accumulation may beselected from the group consisting of overweight, obesity, type 2 diabetes, insulin resistance, hypertension, cardiovascular disease or metabolic syndrome.

Examples of obesity related comorbidities include one or more of insulin resistance, glucose intolerance, diabetes mellitus, hypertension, dyslipidemia, sleep apnea, arthritis, hyperuricemia, gall bladder disease, and certain types of cancer, coronary artery disease, heart failure, cardiac arrhythmia, stroke, and menstrual irregularities.

Adiposity rebound occurs normally from 6 years of age, for example after 6 years of age, or after 7 year, or for example at 7 years; such as in the interval from 6 to 9 years, such as from 6 to 8 years, for example from 6 to 7 years.

In contrast, premature adiposity rebound is defined in the context of this application as adiposity rebound which occurs earlier than it would normally occur. Accordingly, premature adiposity rebound may be said to be for example when adiposity rebound (i.e, the time where BMI begins to rise after infancy) occurs before 6 years of age, for example in the interval from 2 up to 6 years, for example 3 up to 6 years, or for example 4 up to 6 years, or 5 up to 6 years of age, or for example from 2 to 5 years, 3 to 5 years, 4 to 5 years.

Target Groups

The nutritional composition according to the invention is for use in infants or young children.

In some embodiments the nutritional composition according to the invention is for use in infants or young children at risk of developing a later in life health disorder, for example a health disorder related to excessive fat mass accumulation.

The infants or young children may be born term or preterm. In a particular embodiment the nutritional composition of the invention is for use in preterm infants. Pre-term infants may be at increased risk of insulin resistance, hyperglycemia, poor nutrient utilization, impaired lean body mass growth, fat accumulation in the visceral area and metabolic disease later in life. Thus, one embodiment of the present aspect of the invention relates to a nutritional composition for use according to the invention wherein the infant or young child is at risk for obesity, such as one or more selected from the group consisting of pre-term infants, infants born to born to overweight and obese mothers, and/or infants born to mothers carrying the SNP rs3894326.

The nutritional composition of the present invention may also be used in an infant or a young child that was born by C-section or that was vaginally delivered.

The timing for adiposity rebound may vary in subpopulations, or for example in different target groups. Thus, alternatively, premature adiposity rebound may be defined as adiposity rebound which occurs at least 6 months earlier than the average timing of adiposity rebound of a subpopulation. For example, premature adiposity rebound may be defined as adiposity rebound which occurs 8 months earlier, 12 months earlier, 18 months earlier, 24 months earlier than the average time point for a subpopulation. In further examples, premature adiposity rebound may be defined as adiposity rebound which occurs in a period of time from 6 months to 36 months earlier than the average time point for a subpopulation, such from 6 months to 30, 7 months to 24 months, 7 to 20 months, 7 to 18 months, 7 to 16 months, 8 to 12 months earlier than the average time point for a subpopulation.

A subpopulation may be for example a selected target group, such as subpopulation of infants determined to be at risk for overweight and/or obesity later in life. In one embodiment a subpopulation may be infants born to mothers who display one or more of the SNPs. In another embodiment a subpopulation may be infants or young children born to overweight and obese women. Indeed, scientific evidence continues to suggest that infants born to overweight and obese mothers have a greater risk of becoming overweight or obese later in life than infants born to mothers who are not overweight or obese.

Nutritional Composition

Further embodiments of the present aspect of the invention relate to a nutritional composition for use according to the present invention wherein the at least one fucosylated oligosaccharide, for example the at least one fucosylated oligosaccharide with alpha 1,3 and/or alpha 1,4 linkage (or fucosylated oligosaccharide fucosylated by FUT3) is present in an amount of from 0.02 to 10 wt %, such as from 0.1 to 5 wt % or from 0.2 to 1.5 wt % of the nutritional composition, all percentages by dry weight. In some embodiments the at least one fucosylated oligosaccharide is present in a total amount of 0.05 to 1.5 g/L, for example 0.1 g/L or 0.8 g/L of the composition.

In further embodiments, the nutritional composition for use according to the invention comprises or preferably further comprises at least one fucosylated oligosaccharide with alpha 2 linkage and/or alpha 1,2 linkage; and/or which is fucosylated by FUT2. In some embodiments, this nutritional composition comprises one or more fucosylated oligosaccharide selected from the group consisting of alpha 1,2' fucosylated lactose and alpha 2' fucosylated lactose. In a particular embodiment, the nutritional composition for use according to the invention further comprises 2-FL (2' fucosyllactose).

Adapted Nutritional Compositions

The nutritional composition according to the invention may be adapted to meet the needs of an infant or young child. For example, the nutritional composition for use according to the invention may be an infant formula, a starter infant formula, a follow-on or follow-up infant formula, a baby food, an infant cereal composition, a growing-up milk, a fortifier or a supplement.

For example, the nutritional composition for use may be a powdered infant formula that is diluted with water to give a final liquid product. In other examples, the nutritional composition for use according to the invention may also be a concentrated liquid that is diluted with water to achieve the final liquid product. The nutritional composition for use according to the invention may be a liquid product that is directly consumed by the infant as it is. The nutritional composition according to the invention may be a human milk fortifier that is added to or diluted with human milk. In this case, the concentration of the components already present in the human milk (to which the human milk fortifier is added) are to be taken as the average values for lactating mothers that are known or predicted from published clinical data.

The nutritional composition for use according to the present invention may contain a source of lipids. The lipid source may be any lipid or fat which is suitable for use in infant formulae. Preferred fat sources include palm oleic, high oleic sunflower oil and high oleic sunflower oil. The essential fatty acids linoleic and α-linolenic acid may also be added. In the composition, the fat source (including optional LC-PUFA such as ARA and/or DHA) preferably has a ratio of n-6 to n-3 fatty acids of about 1:2 to about 10:1, preferably about 5:1 to about 10:1, even more preferably about 7:1 to about 9:1.

The nutritional composition according to the invention is preferably such that the fat consists essentially of a mixture of 0 to 20% of milk fat; 10 to 30% of coconut oil; 10 to 40% of canola oil; 10 to 25% sunflower oil; 10 to 30% of high oleic sunflower oil; 2 to 10% of palmitic acid mainly in the form of triglycerides; and 1,5 to 2,5% of a mixture of poly-unsaturated fatty acids ARA and DHA (such as a mixture in 1:1 proportion of ARASCO® and DHASCO® from Martek), preferably in a ratio ARA:DHA of about 1:1, with respect to the total fat.

The milk fat could be replaced efficiently by Betapol®, or by Infat® from AAK/Enzymotec.

Each one of these fat sources is a refined oil suitable for infant nutrition applications.

Other standard ingredients known to the skilled person for formulating infant formula, a starter infant formula, a follow-on or follow-up infant formula, a baby food, an infant cereal composition, a growing up milk, a fortifier or a supplementmay also be present in the nutritional compositions for use according to the invention.

Thus, the nutritional composition for use according to the invention may contain other ingredients which may act to enforce the technical effect of the components, particularly according to the Commission Directive 2006/141/EC of 22 Dec. 2006 on infant formulae and follow-on formulae.

The nutritional composition for use according to the present invention may also contain a carbohydrate source, preferably as prebiotics, or in addition to prebiotics. Any carbohydrate source conventionally found in infant formulae such as lactose, saccharose, maltodextrin, starch and mixtures thereof may be used although the preferred source of carbohydrates is lactose.

The prebiotics that may be included in accordance with the present invention are not particularly limited and include all food substances that promote the growth of probiotics or health beneficial micro-organisms in the intestines. Preferably, they may be selected from the group consisting of oligosaccharides, optionally containing fructose, galactose, and mannose; dietary fibers, in particular soluble fibers, soy fibers; inulin; or mixtures thereof. Some examples of prebiotics are fructo-oligosaccharides (FOS), galacto-oligosaccharides (GOS), isomalto-oligosaccharides (IMO), xylo-oligosaccharides (XOS), arabino-xylo oligosaccharides (AXOS), mannan-oligosaccharides (MOS), inulin, polydextrose oligosaccharides of soy, glycosylsucrose (GS), lactosucrose (LS), lactulose (LA), palatinose-oligosaccharides (PAO), malto-oligosaccharides, gums and/or hydrolysates thereof, pectins and/or hydrolysates thereof. In a particular embodiment, the prebiotics may be fructooligosaccharides and/or inulin. In a specific embodiment, the prebiotics is a combination of FOS with inulin such as in the product sold by BENEO-Orafti under the trademark Orafti® oligofructose (previously Raftilose®) or in the product sold by BENEO-Orafti under the trademark Orafti® inulin (previously Raftiline®). Another example is a combination of 70% short chain fructo-oligosaccharides and 30% inulin, which is registered by Nestle under the trademark "Prebio 1".

The prebiotics can also be a BMO (bovine's milk oligosaccharide) and/or a HMO (human milk oligosaccharide) such as N-acetylated oligosaccharides, sialylated oligosaccharides, other fucosylated oligosaccharides and any mixtures thereof.

Particular embodiments relate to the nutritional composition according to the invention further comprising at least one further oligosaccharide(s) and/or fiber(s) and/or precursor(s) of human milk oligosaccharides selected from the list comprising GOS, FOS, XOS, inulin, polydextrose, sialylated oligosaccharides, sialic acid, fucose, N-acetylated oligosaccharides and any combination thereof.

A particular example of prebiotic is a mixture of galacto-oligosaccharide(s), N-acetylated oligosaccharide(s) and sialylated oligosaccharide(s) in which the N-acetylated oligosaccharide(s) represent 0.5 to 4.0% of the oligosaccharide mixture, the galacto-oligosaccharide(s) represent 92.0 to 99.5% of the oligosaccharide mixture and the sialylated oligosaccharide(s) represent 1.0 to 4.0% of the oligosaccharide mixture. This oligosaccharide mixture is preferably a mixture of BMOS (bovine milk oligosaccharides) For example a composition for use according to the invention can contain from 2.5 to 15.0 wt % of this BMOS mixture on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide. WO2006087391 and WO2012160080 provide some examples of production of this BMOs mixture.

The nutritional composition for use according to the present invention may further comprise one or more probiotics. In particular embodiments, the one or more probiotics may be selected for this purpose from the group consisting of *Bifidobacterium, Lactobacillus, Lactococcus, Enterococcus, Streptococcus, Kluyveromyces, Saccharoymces, Candida*, in particular selected from the group consisting of *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus lactis, Lactobacillus rhamnosus, Lactobacillus johnsonii, Lactobacillus plantarum, Lactobacillus salivarius, Lactococcus lactis, Enterococcus faecium, Saccharomyces cerevisiae, Saccharomyces boulardii* or mixtures thereof. Some suitable examples of probiotics are selected from the group consisting of *Bifidobacterium longum* NCC3001 (ATCC BAA-999), *Bifidobacterium longum* NCC2705 (CNCM I-2618), *Bifidobacterium longum* NCC490 (CNCM I-2170), *Bifidobacterium lactis* NCC2818 (CNCM I-3446), *Bifidobacterium breve* strain A, *Lactobacillus paracasei* NCC2461 (CNCM I-2116), *Lactobacillus johnsonii* NCC533 (CNCM I-1225), *Lactobacillus rhamnosus* GG (ATCC53103), *Lactobacillus rhamnosus* NCC4007 (CGMCC 1.3724), *Enterococcus faecium* SF 68 (NCC2768; NCIMB10415), and mixtures thereof.

The nutritional composition for use according to the present invention may also contain a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. The proteins can be at least partially hydrolyzed in order to enhancement of oral tolerance to allergens, especially food allergens. In that case the composition is a hypoallergenic composition.

In a preferred embodiment, the composition may be cow's milk whey based infant formula. The formula may also be a hypoallergenic (HA) formula in which the cow milk proteins are (partially or extensively) hydrolysed. The formula may also be based on soy milk or a non-allergenic formula, for example one based on free amino acids.

The protein can be in an amount of from 1.5 to 3 g per 100 kcal. A particular embodiment relates to a nutritional composition for use according to the present invention wherein the protein content is less than 2 g/100 kcal, for example 1 to 2 g/100 kcal; such as such as less than 1.8 g/100 kcal, for example 1 to 1,8 g/100 kcal; for example in the range from 1.5 to 1.8 g protein/100 kcal.

The nutritional composition for use according to the present invention may also contain all vitamins and minerals, and other micronutrients, understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition for use according to the present invention may contain emulsifiers and stabilisers such as soy, lecithin, citric acid esters of mono- and di-glycerides, and the like.

The nutritional composition for use according to the present invention may also contain other substances which may have a beneficial effect such as lactoferrin, nucleotides, nucleosides, gangliosides, polyamines, and the like.

The preparation of nutritional composition for use according to the present invention will now be described by way of example.

The formula may be prepared in any suitable manner. For example, it may be prepared by blending together a protein source, a carbohydrate source, and a fat source, in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) may be added at this stage, especially if the final product is to have a liquid form. If the final product is to be a powder, they may likewise be added at this stage if desired.

The liquid mixture is then homogenized, for example in two stages.

The liquid mixture may then be thermally treated to reduce bacterial loads, by rapidly heating the liquid mixture to a temperature in the range between about 80° C. and about 150° C. for duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenized, for example in two stages between about 10 MPa and about 30 MPa in the first stage and between about 2 MPa and about 10 MPa in the second stage. The homogenized mixture may then be further cooled to add any heat sensitive components, such as vitamins and minerals. The pH and solids content of the homogenized mixture are conveniently adjusted at this point.

The homogenized mixture is transferred to a suitable drying apparatus such as a spray dryer or freeze dryer and converted to powder. The powder should have a moisture content of less than about 5% by weight. The fucosylated oligosaccharide(s) may also or alternatively be added at this stage by dry-mixing along with optional probiotic bacterial strain(s), or by blending them in a syrup form of crystals, along with optional probiotic bacterial strain(s), and spray-dry (or freeze-dry).

If a liquid composition is preferred, the homogenized mixture may be sterilized then aseptically filled into suitable containers or may be first filled into the containers and then retorted.

In another embodiment, the composition of the invention may be a supplement in an amount sufficient to achieve the desired effect in an infant. This form of administration is usually more suited to preterm infants.

The supplement may be in the form of powder, tablets, capsules, pastilles or a liquid for example, as long as it is a suitable nutritional composition for the infant. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

The supplement can be added in a product acceptable to the consumer (who is an infant), such as an ingestible carrier or support, respectively. Examples of such carriers or supports are a pharmaceutical or a food composition. Examples for such compositions are infant formula including preterm formula.

Further, the supplement may contain an organic or inorganic carrier material suitable for enteral or parenteral administration as well as vitamins, minerals trace elements and other micronutrients in accordance with the recommendations of Government bodies such as the European Commission Directive 2006/141/EC of 22 Dec. 2006 on infant formulae and follow-on formulae.

Dosage Regime

The nutritional composition for use according to the invention may be given at any period during infancy and young childhood. The nutritional composition can be administered (or given or fed) at an age and for a period that depends on the possibilities and needs.

In one embodiment of the present aspect of the invention, the nutritional composition for use according to the invention is administered when the infant or young child is of an age from birth to 3 years, such as from 6 months to 3 years, 7 months to 3 years, 8 months to 3 years, 9 months to 3 years, 10 months to 3 years, 12 months to 3 years, or for example from 1 year to 3 years or 2 years to 3 years. Particular embodiments relate to wherein the infant or young child is from 8 months to 3 years.

Since the nutritional composition is mainly used for prevention purposes (avoiding excessive fat mass accumulation, preventing a later in life health disorder related to excessive fat mass accumulation like obesity later in life), it can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

Use for Overweight

The invention relates in another aspect to the use of a nutritional composition as defined herein in context of the aspect of a nutritional composition for use, for reducing the risk of development of overweight later in life in an infant or a young child by preventing premature adiposity rebound.

Nutritional Composition for Use to Promote Healthy Growth

In a further aspect, the invention relates to a nutritional composition comprising at least one fucosylated oligosaccharide for use to promote healthy growth by preventing premature adiposity rebound.

One embodiment relates to a nutritional composition according to the invention comprising one or more of a fucosylated oligosaccharide having at least one fucose group attached by an alpha 1,3 linkage, by an alpha 1,4 linkage, and/or by an alpha 1,2 or alpha 2 linkage.

One embodiment relates to a nutritional composition according to the invention having at least one fucose group attached by an alpha 1,3 linkage, at least one fucose group attached by an alpha 1,4 linkage, or combinations thereof, for use to promote healthy growth in an infant or young child.

The expression "growth" refers to growth in weight, height, head and/or abdominal circumference of an infant or young child. In a particular embodiment it refers to the weight. The growth has to be understood as the evolution of the weight, height, head and/or abdominal circumference over the aging of the infant or young child. So the expressions "growth rate" and "rate of growth" can also be used alternatively to the term "growth". These parameters do not exclusively increase during development of the infant, as indeed the standard curves of growth published by the WHO show that the weight of an infant may decrease in the first days of life of the infant. Therefore, the growth has to be understood as the overall growth of the infant over the first months of life, such as in particular from birth to 8 months, birth to 10 months, birth to 12 months, or birth to 24 months, or birth to 36 months.

The expressions "promoting a healthy growth" and "promoting an optimal growth" can be used interchangeably. They encompasses promoting a rate of growth which gets closer or approximates to the rate of growth of a breast-fed infant. They encompass promoting a growth that is qualified as normal by pediatricians so that it is not associated with providing health issues. These expressions also encompass preventing excessive growth or excessive body weight gain that may occur in formula-fed infants, especially in the first few months of life. The expression "promoting a healthy growth" may also encompass controlling weight management and/or avoiding weight gain, especially excessive weight gain, and/or promoting a lean mass increase, especially over a total weight or adipose mass increase.

One embodiment of this aspect relates to a nutritional composition comprising at least one fucosylated oligosaccharide which is fucosylated by FUT3 for use to promote healthy growth in an infant or young child, by preventing premature adiposity rebound.

In particular embodiments, the nutritional composition according to the invention for use to promote healthy growth in an infant or young child, wherein the infant or young child may be as described herein above under the heading Target groups.

In further embodiments, the nutritional composition for use according to this aspect may be as described herein above in relation to previous aspects of the invention.

Methods of Identifying Target Groups

The presence of a FUT3 polymorphism which disturbs the expression of FUT3 leads to reduced amounts of fucosylated oligosaccharide having at least one fucose group attached by an 1,3 linkage and/or at least one fucose group attached by an 1,4 linkage. Based on the association identified between abdominal circumference and this FUT3 polymorphism, such infants may be identified as at risk for premature adiposity rebound and/or excessive fat mass accumulation.

Accordingly, the invention relates in a further aspect to a method of identifying whether an infant or young child is at risk for excessive fat mass accumulation and/or for one or more health disorders, such as a health disorder related to excessive fat accumulation, either in the infancy/young childhood or later in life; said method comprising determining the presence of the following single nucleotide polymorphism in the FUT3 gene in the mother of the infant:

a) rs3894326 (Deposit number at SNP database, MCBI)
wherein the presence of said polymorphism is associated with increased risk of premature adiposity rebound, excessive fat mass accumulation and for one or more health disorders, such as a health disorder related to excessive fat accumulation, in the infancy and/or later in the life of the infant.

The numbers of the polymorphism refers to the deposit number at Single Nucleotide Polymorphism database, at NCBI and available online.

Method of Treatment

Mothers who display the disrupted FUT3 gene will produce less fucosylated oligosaccharide with at least one fucose attached via alpha 1,3 and/or alpha 1,4 linkages. In order to compensate for this lack, it would be advantageous to identify mothers which are lacking in this respect, and to supplement the diet of their offspring with at least one such fucosylated oligosaccharide.

Thus, a further aspect of the present invention relates to a method for prevention of premature adiposity rebound, excessive fat accumulation and/or a health disorder related to excessive fat mass accumulation later in the life of an infant or young child comprising the steps of
  i. Determining whether a mother has a functional FUT3 enzyme or not, and
  ii. Administering to said infant or young child a nutritional composition as defined above in context of the nutritional composition according to the invention, for example a nutritional composition comprising at least one fucosylated oligosaccharide wherein said fucosylated oligosaccharide has at least one fucose group attached by an alpha 1,3 linkage, at least one fucose group attached by an alpha 1,4 linkage, or combinations thereof, thereby preventing premature adiposity rebound.

The FUT3 enzyme is functional if it results in alpha 1,3 and/or alpha 1,4 fucosylsation of its substrates. Methods of determining whether a mother has a functional FUT3 enzyme or not are known in the art. For example, the gene may be detected by PCR, or functional protein assayed for by immunobased methods, such as western blot.

In one embodiment, the present invention relates to a method for prevention of premature adiposity rebound, excessive fat accumulation and/or a health disorder related to excessive fat mass accumulation later in the life of an infant or young child comprising the steps of
  i. Determining whether a mother has the following single nucleotide polymorphism in the FUT3 gene:
    a) rs3894326
    and
  ii. Administering to said infant or young child a nutritional composition as defined above in context of the nutritional composition according to the invention, for example a nutritional composition comprising at least one fucosylated oligosaccharide wherein said fucosylated oligosaccharide has at least one fucose group attached by an alpha 1,3 linkage, at least one fucose group attached by an alpha 1,4 linkage, or combinations thereof, thereby preventing premature adiposity rebound.

For Use in Manufacture

The aspect of the invention relating to a nutritional composition for use according to the invention, may alternatively be described as the use of a fucosylated oligosaccharide, for the manufacture of a nutritional composition for administration to an infant or young child for reducing and/or avoiding later in life excessive fat mass accumulation; and/or for preventing a later in life health disorder, such as a health disorder related to fat accumulation, by preventing premature adiposity rebound, and/or by regulating timing of adiposity rebound.

A further embodiment relates to the use of a fucosylated oligosaccharide which is fucosylated by FUT3 for the manufacture of a nutritional composition for administration to an infant or young child for reducing and/or avoiding later in life excessive fat mass accumulation; and/or for in preventing a later in life health disorder, such as a later in life health disorder related to fat accumulation by preventing premature adiposity rebound.

A further embodiment relates to the use of a fucosylated oligosaccharide which is fucosylated by FUT3 for the manufacture of a nutritional composition for reducing and/or preventing excessive fat mass accumulation in an infant or a young child; and/or for in preventing a later in life health disorder related to fat accumulation in an infant or young child by preventing premature adiposity rebound.

Yet further embodiments relate to said use of a fucosylated oligosaccharide, wherein the nutritional composition is defined as described herein above in relation to a nutritional composition for use according to the invention.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

An example of the composition of a nutritional composition (e.g. an infant formula) according to the present invention is given in the below table 2. This composition is given by way of illustration only.

TABLE 2 an example of the composition of a nutritional composition (e.g. an infant formula) according to the present invention

| Nutrients | | per 100 kcal | per litre |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 11.2 | 74.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (µg) | | 8 | 50 |
| Se (µg) | | 2 | 13 |
| Vitamin A (µg RE) | | 105 | 700 |
| Vitamin D (µg) | | 1.5 | 10 |
| Vitamin E (mg TE) | | 0.8 | 5.4 |
| Vitamin K1 (µg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides (HMOs) | DFL (g) | 0.015 | 0.1 |

Example 2: Association of SNP with Growth

The oligosaccharide profile of human milk depends on the genetic variations of e.g. enzymes involved in glycosylation. The inventors have studied whether the variation in oligosaccharide influence child health. An association study between FUT3 SNP and child health outcomes was performed. SNP analysis of maternal samples from a population cohort was performed, and logistic regression analysis was used to determine associations between FUT3 SNP and child health outcomes. Significant association between the LMS growth scores and FUT3 SNP was uncovered. LMS growth score method is known in the art (see Eur J Clin Nutr. 1990 January; 44(1):45-60, The LMS method for constructing normalized growth standards, Cole T J). Although LMS is typically seen as a cross/sectional method it can be used on longitudinal data.

Association between LMS growth scores and FUT3 SNP has been investigated for growth in abdominal circumference for the periods of time, and the results are shown in Table 3 below.

Where SNP was found to be significantly associated with outcomes, the regression models were further adjusted (see Table 3) for parity, mode of delivery and breastfeeding.

There is an association between LMS abdominal circumference growth scores from 6 to 12 months and FUT3 SNP rs3894326 (p=0.043). This association remains significant when adjusted for breastfeeding, parity and mode of delivery; with breastfeeding duration (0, <=3 m, >3 m) also showing a significant association with LMS AC growth.

Abdominal circumference growth from 2 to 3 years is also significantly associated with FUT3 SNP rs3894326

As conditional z score for a growth outcome or size such as abdominal adiposity, is defined as this size regressed on total body size described by (Keijzer-Veen et al., 2005).

In Table 3, data for both unadjusted and adjusted model are shown.

Abbreviations and Comments

LMS growth score is a measure for abdominal circumference (AC) as defined above.

SNP means single nucleotide polymorphism, in this case it is rs3894326.

N is the number of participants in the study.

Figure 2:
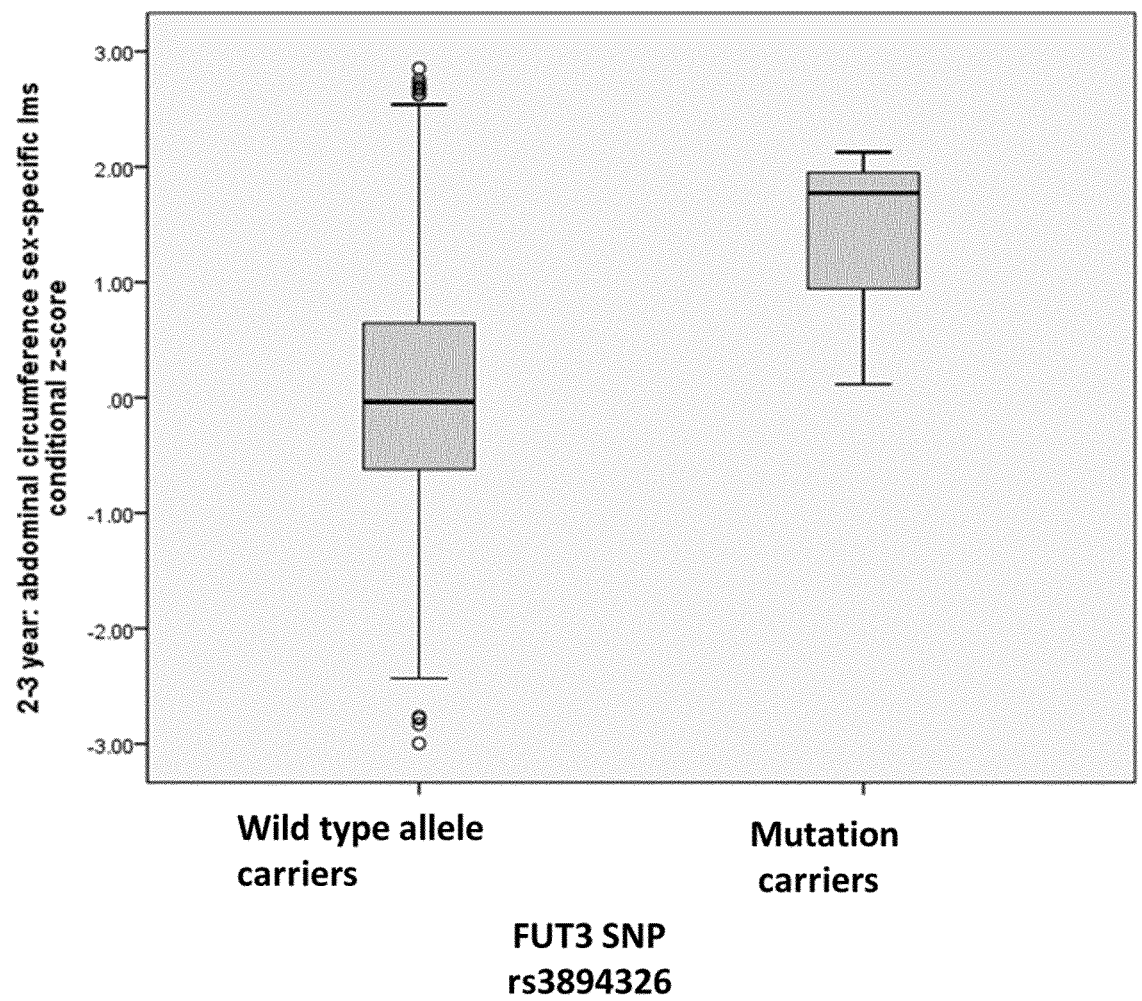
FIG. 2 shows the abdominal circumference sex-specific LMS conditional z-score for 2-3 years for the polymorphism FUT3 rs3894326.

Beta is the beta value coefficient of the regression model used in the analysis. Negative beta value for AC, 6 to 12 months shows that the group of infants with a mother carrying the mutation type SNP is associated with lower AC compared to those with a mother carrying the wild type SNP, whereas the positive beta value for AC, 2 to 3 years shows that the group of infants with a mother carrying the mutation type SNP is associated with higher AC compared to those with a mother carrying the wild type SNP, as depicted in FIGS. 1 and 2.

AC=abdominal circumference; m=months; yrs=years. Adjusted=see description of Example above.

TABLE 3

| LMS growth score | SNP | N | Beta | P value | N (adjusted) | Beta (adjusted) | P value (adjusted) | Other significant predictors |
|---|---|---|---|---|---|---|---|---|
| AC 6 to 12 m | rs3894326 (FUT3) | 564 | −0.988 | 0.043 | 659 | −1.014 | 0.043 | breastfeeding |
| AC 2 to 3 yrs | rs3894326 (FUT3) | 450 | 1.363 | 0.018 | 518 | 1.313 | 0.023 | none |

(p=0.018), which remains significant when adjusted for breastfeeding duration, parity and mode of delivery. The results show that the presence of the form of FUT3 SNP rs3894326 disrupting the FUT3 gene (carrying the mutation) is associated with reduced abdominal circumference at 6 months and increased abdominal circumference at 2 to 3 years of age compared to the form of the SNP with no impact on FUT3 gene (wild type). This means that absence of a functional FUT3 enzyme and as a result no production of alpha 1,3 and 1,4 fucosylated HMOs is associated with a higher abdominal circumference, a measure of adiposity, in 2 to 3 years. An early higher adiposity rebound in 2 to 3 years for the group of infants fed with human milk with reduced amount of alpha 1, 3 and 1, 4 fucosylated HMOs (non-functional FUT3 enzyme) predisposes to future fat accumulation-related disorders; therefore it is concluded that alpha 1, 3 and 1, 4 fucosylated HMOs are necessary for optimal growth of the infants, and that their presence prevents premature adiposity rebound.

In FIG. 1, the conditional z score of abdominal circumference at 6 to 12 is shown between the infants with a mother carrying the fully functional FUT3 form (SNP rs3894326: AA, wild type) and the infants carrying the altered FUT3 form (SNP rs3894326: TA, carrying mutation). In FIG. 2, the conditional z scores of abdominal circumference for the same groups of infants are shown for 2 to 3 years. It is clear that for infants born in mothers with a non-fully functional FUT3 and thus a reduced amount of 1, 3 and alpha 1, 4 fucosylated HMOs in milk could disrupt normal infant growth.

The invention claimed is:

1. A method for preventing a later in life health disorder in an infant born to a mother carrying single nucleotide polymorphism (SNP) rs3894326, by preventing premature adiposity rebound, the method comprising administering an effective amount of a synthetic nutritional composition comprising diFucosyllactose (DFL) to the infant, wherein the DFL is 0.2 to 1.5 wt % of the synthetic nutritional composition by dry weight.

2. The method according to claim 1, wherein the later in life health disorder is related to excessive fat mass accumulation.

3. The method according to claim 1, wherein the synthetic nutritional composition further comprises at least one additional fucosylated oligosaccharide selected from the group consisting of 3' fucosylated lactose (3'FL), Lacto-N-fucopentaose II (LNFP II), Lacto-N-fucopentaose III (LNFP III), Lacto-N-fucopentaose V (LNFP V), and combinations thereof.

4. The method according to claim 1, wherein the health disorder is selected from the group consisting of overweight, obesity, type 2 diabetes, insulin resistance, hypertension, cardiovascular disease and metabolic syndrome.

5. The method according to claim 1, wherein the synthetic nutritional composition further comprises at least one ingredient selected from the group consisting of galacto-oligosaccharides (GOS), fructo-oligosaccharides (FOS), xylo-oligosaccharides (XOS), inulin, polydextrose, sialylated oligosaccharides, sialic acid, fucose, N-acetylated oligosaccharides and combinations thereof.

6. The method according to claim 1, wherein the synthetic nutritional composition further comprises at least one probiotic in an amount from $10^3$ to $10^{12}$ cfu/g of the synthetic nutritional composition by dry weight.

7. The method according to claim 1, wherein the synthetic nutritional composition is in a form selected from the group consisting of an infant formula, a starter infant formula, a follow-on or follow-up infant formula, a baby food, an infant cereal composition, a growing-up milk, a fortifier and a supplement.

8. A method for preventing premature adiposity rebound in an infant born to a mother carrying single nucleotide polymorphism (SNP) rs3894326, the method comprising administering to the infant an effective amount of a synthetic nutritional composition comprising diFucosyllactose (DFL), wherein the DFL is 0.2 to 1.5 wt % of the synthetic nutritional composition by dry weight.

9. The method according to claim 1, wherein the synthetic nutritional composition further comprises a source of lipids, a source of proteins and a source of carbohydrates.

10. The method according to claim 9, wherein the source of lipids is selected from the group consisting essentially of palm oleic, sunflower oil, high oleic sunflower oil, coconut oil, canola oil, a mixture of poly-unsaturated fatty acids of arachidonic acid (ARA) and docosahexaenoic acid (DHA), milk fat and combinations thereof.

11. The method according to claim 1, wherein the synthetic nutritional composition further comprises an ingredient selected from the group consisting of a vitamin, a mineral, an emulsifier, a stabilizer, a lactoferrin, a nucleotide, a nucleoside, a ganglioside, a polyamine and combinations thereof.

12. The method according to claim 1, wherein the synthetic nutritional composition is in a physical form selected from the group consisting of a powder, a tablet, a capsule, a pastille and a liquid.

13. The method according to claim 1, wherein the synthetic nutritional composition further comprises a source of prebiotics.

* * * * *